US012648703B2

(12) United States Patent
Kobayashi et al.

(10) Patent No.: US 12,648,703 B2
(45) Date of Patent: Jun. 9, 2026

(54) BIOLOGICAL FLUID INFORMATION ACQUISITION APPARATUS

(71) Applicant: SEIKO EPSON CORPORATION, Tokyo (JP)

(72) Inventors: Hiroki Kobayashi, Hara-Mura (JP); Ayae Sawado, Kai (JP); Tsukasa Eguchi, Matsumoto (JP)

(73) Assignee: SEIKO EPSON CORPORATION (JP)

( * ) Notice: Subject to any disclaimer, the term of this patent is extended or adjusted under 35 U.S.C. 154(b) by 0 days.

(21) Appl. No.: 19/092,143

(22) Filed: Mar. 27, 2025

(65) Prior Publication Data

US 2025/0302321 A1    Oct. 2, 2025

(30) Foreign Application Priority Data

Mar. 28, 2024    (JP) ................................. 2024-053369

(51) Int. Cl.
A61B 5/024        (2006.01)
A61B 5/026        (2006.01)

(52) U.S. Cl.
CPC ........ A61B 5/02427 (2013.01); A61B 5/0261 (2013.01); A61B 2562/0233 (2013.01)

(58) Field of Classification Search
CPC .............. A61B 5/02427; A61B 5/0261; A61B 2562/0233
See application file for complete search history.

(56) References Cited

U.S. PATENT DOCUMENTS

2017/0179682 A1*    6/2017    Ishii ...................... A61B 5/0261
2022/0296109 A1*    9/2022    Eguchi ................. A61B 5/0261

FOREIGN PATENT DOCUMENTS

JP        2022-144578 A    10/2022

* cited by examiner

*Primary Examiner* — Chao Sheng
(74) *Attorney, Agent, or Firm* — Harness, Dickey & Pierce, P.L.C.

(57)            ABSTRACT

A biological fluid information acquisition apparatus includes a light source, a prism, a first light receiving element, a second light receiving element, a differential circuit, and a signal processing unit. The prism has a first boundary face that branches a laser beam emitted from the light source into a first luminous flux and a second luminous flux, a second boundary face that totally reflects the second luminous flux, a third boundary face that totally reflects the second luminous flux reflected by the second boundary face, and a fourth boundary face emitting the second luminous flux reflected by the third boundary face, and, when a width direction of the biological fluid information acquisition apparatus is an X direction and a thickness direction of the biological fluid information acquisition apparatus orthogonal to the X direction is a Y direction, an interval between the second boundary face and the third boundary face in the Y direction is shorter than an interval between the first boundary face and the fourth boundary face in the X direction.

9 Claims, 8 Drawing Sheets

*FIG. 3*

BIOLOGICAL FLUID INFORMATION ACQUISITION APPARATUS

The present application is based on, and claims priority from JP Application Serial Number 2024-053369, filed Mar. 28, 2024, the disclosure of which is hereby incorporated by reference herein in its entirety.

BACKGROUND

1. Technical Field

The present disclosure relates to a biological fluid information acquisition apparatus.

2. Related Art

In related art, a biological information acquisition apparatus that acquires biological fluid information including a blood flow volume, a blood volume, a blood flow velocity, a pulse rate, and the like in a biological tissue using scattered light from a biological tissue is known (for example, see JP-A-2022-144578).

The biological information acquisition apparatus disclosed in JP-A-2022-144578 includes a light source that emits a laser beam, an optical branching element that branches the laser beam into a first luminous flux and a second luminous flux, a first light receiving element that receives the first luminous flux, a second light receiving element that receives scattered light of the second luminous flux entering a site to be examined of a living body, a differential circuit to which the first light receiving element and the second light receiving element are coupled, a signal processing unit that obtains biological fluid information by processing a light detection signal output via the differential circuit, and a first light shielding section that reduces the incidence of the scattered light on the first light receiving element.

In the biological information acquisition apparatus, optical branching for differential amplification, return light prevention for noise reduction, oblique irradiation, and the like are respectively performed by independent elements.

JP-A-2022-144578 is an example of the related art.

In the biological information acquisition apparatus disclosed in JP-A-2022-144578, each function is achieved by a plurality independent elements, and accordingly, the apparatus is upsized and difficult to be a wearable apparatus.

SUMMARY

A biological fluid information acquisition apparatus according to an aspect of the present disclosure includes a light source emitting a laser beam, a prism branching the laser beam emitted from the light source into a first luminous flux and a second luminous flux, a first light receiving element receiving the first luminous flux, a second light receiving element receiving a scattered light obtained from a living body when the second luminous flux enters a site to be examined of the living body, a differential circuit generating a light detection signal based on output of the first light receiving element and the second light receiving element, and a signal processing unit generating biological fluid information by processing the light detection signal, wherein the prism has a plate-like shape or a columnar shape, the prism has a first boundary face that branches the laser beam emitted from the light source into the first luminous flux and the second luminous flux, a second boundary face that totally reflects the second luminous flux, a third boundary face that totally reflects the second luminous flux reflected by the second boundary face, and a fourth boundary face emitting the second luminous flux reflected by the third boundary face, and, when a width direction of the biological fluid information acquisition apparatus is an X direction and a thickness direction of the biological fluid information acquisition apparatus orthogonal to the X direction is a Y direction, an interval between the second boundary face and the third boundary face in the Y direction is shorter than an interval between the first boundary face and the fourth boundary face in the X direction.

BRIEF DESCRIPTION OF THE DRAWINGS

FIG. 3 is a side view of a prism of the biological fluid information acquisition apparatus shown in FIG. 1 as seen from a Z direction.

DESCRIPTION OF EMBODIMENTS

As below, a biological fluid information acquisition apparatus of the present disclosure will be described in detail based on an embodiment shown in the accompanying drawings.

Embodiments

Figure 1:
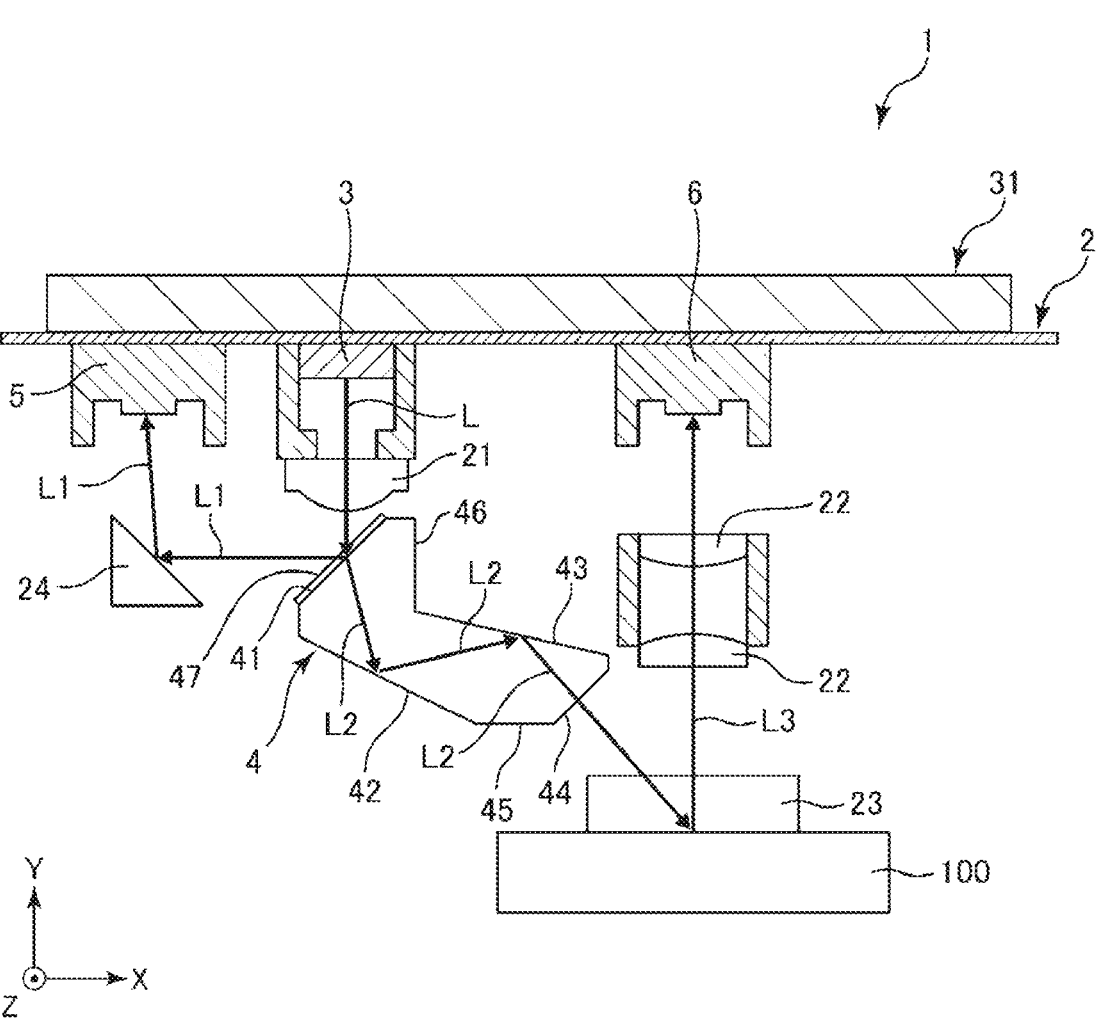
FIG. 1 shows a main part of a biological fluid information acquisition apparatus of the present disclosure in an embodiment.
Figure 2:
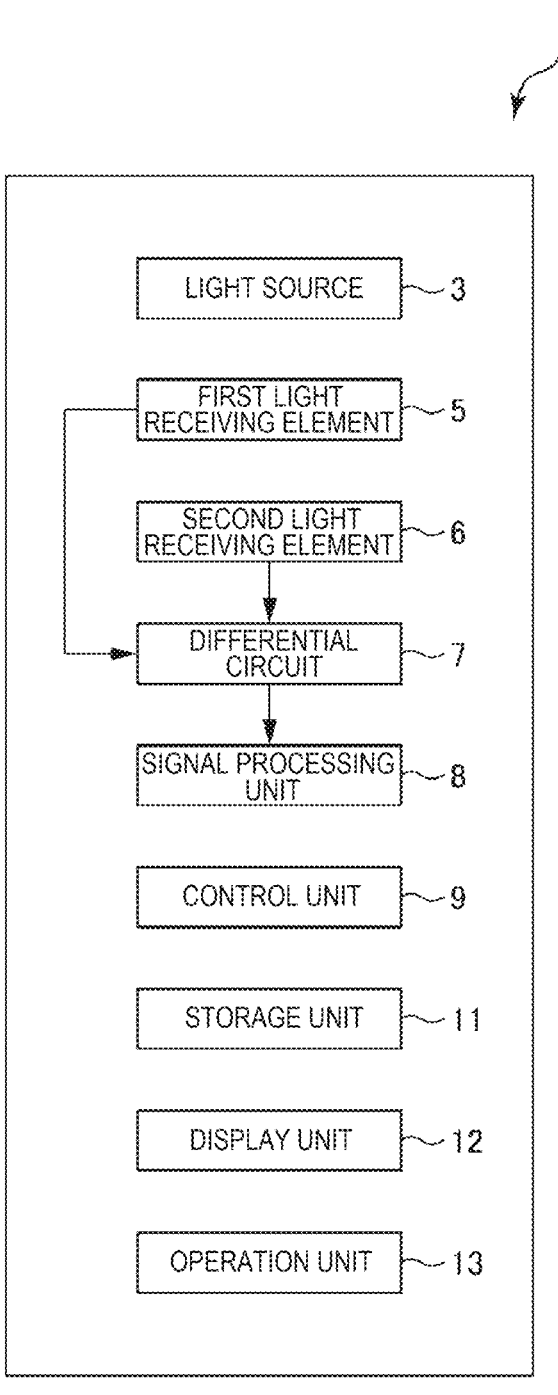
FIG. 2 is a block diagram of the biological fluid information acquisition apparatus shown in FIG. 1.
Figure 3:
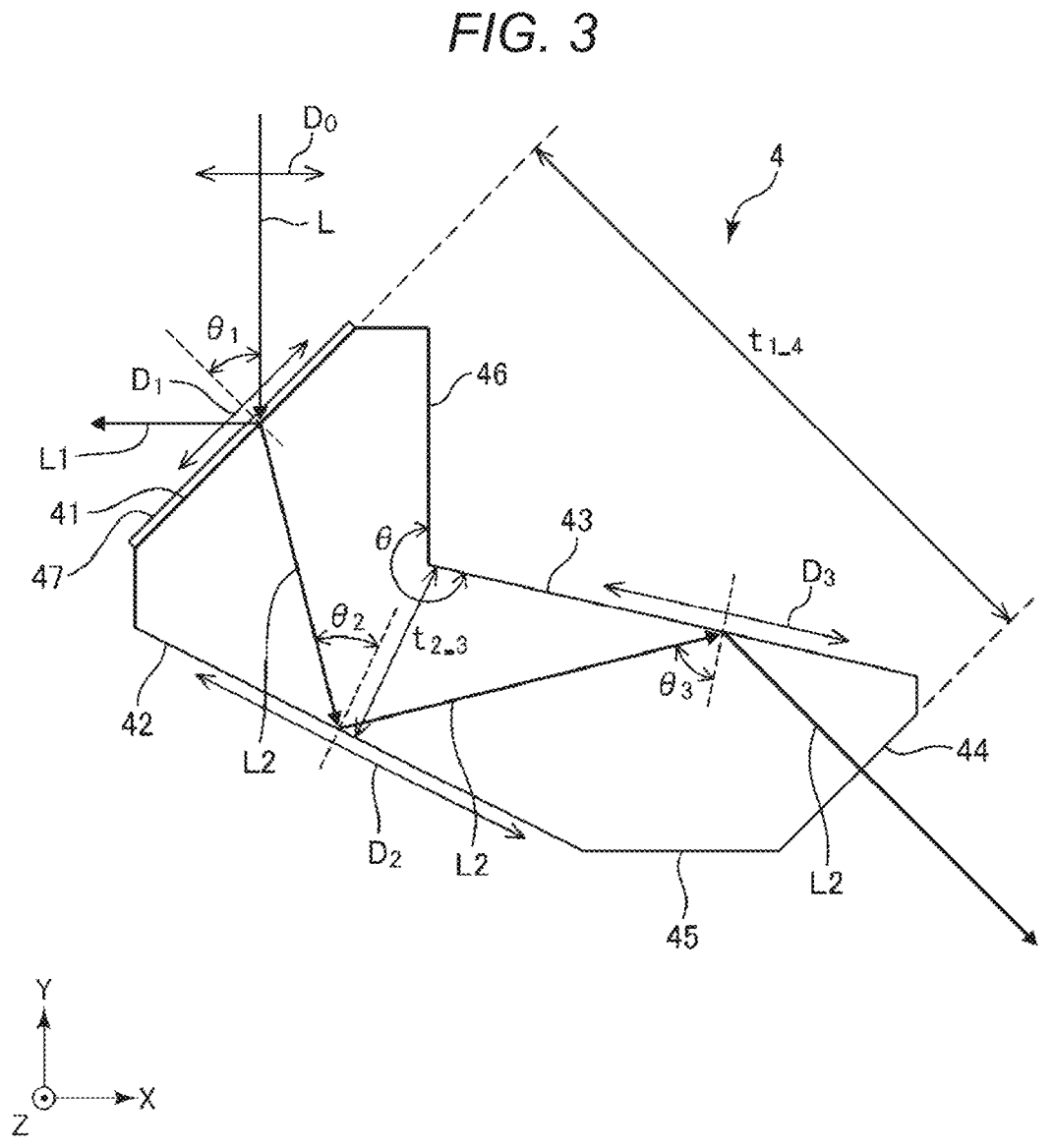
Figure 4:
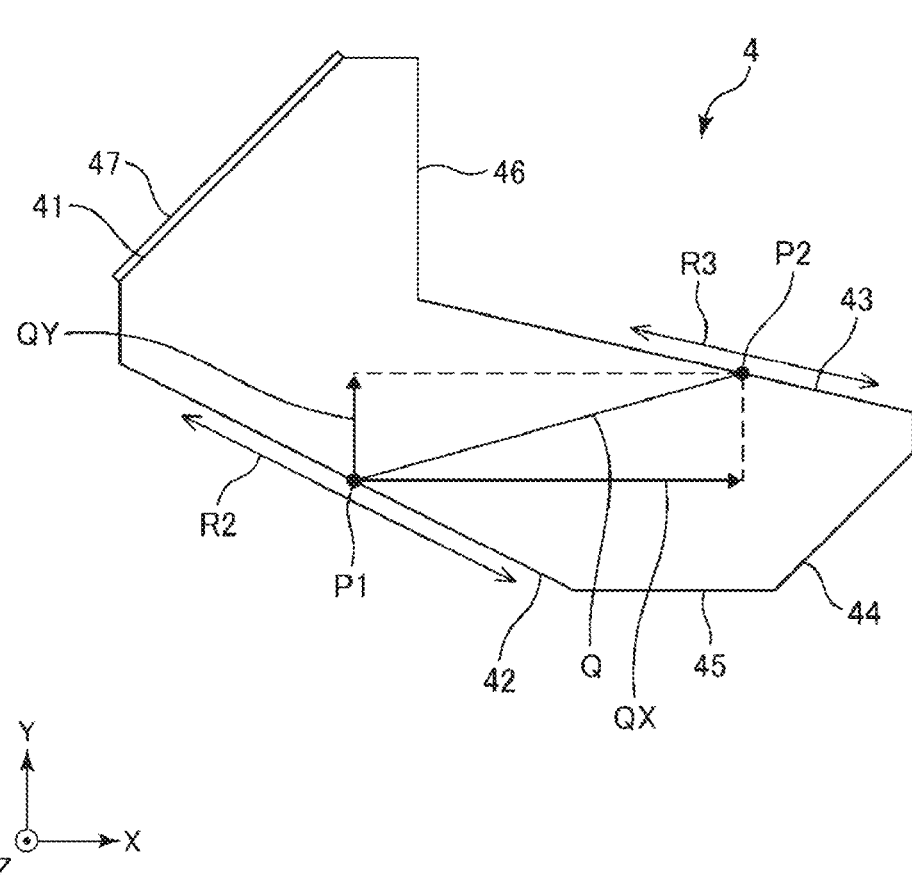
FIG. 4 is a side view of the prism of the biological fluid information acquisition apparatus shown in FIG. 1 as seen from the Z direction.
Figure 5:
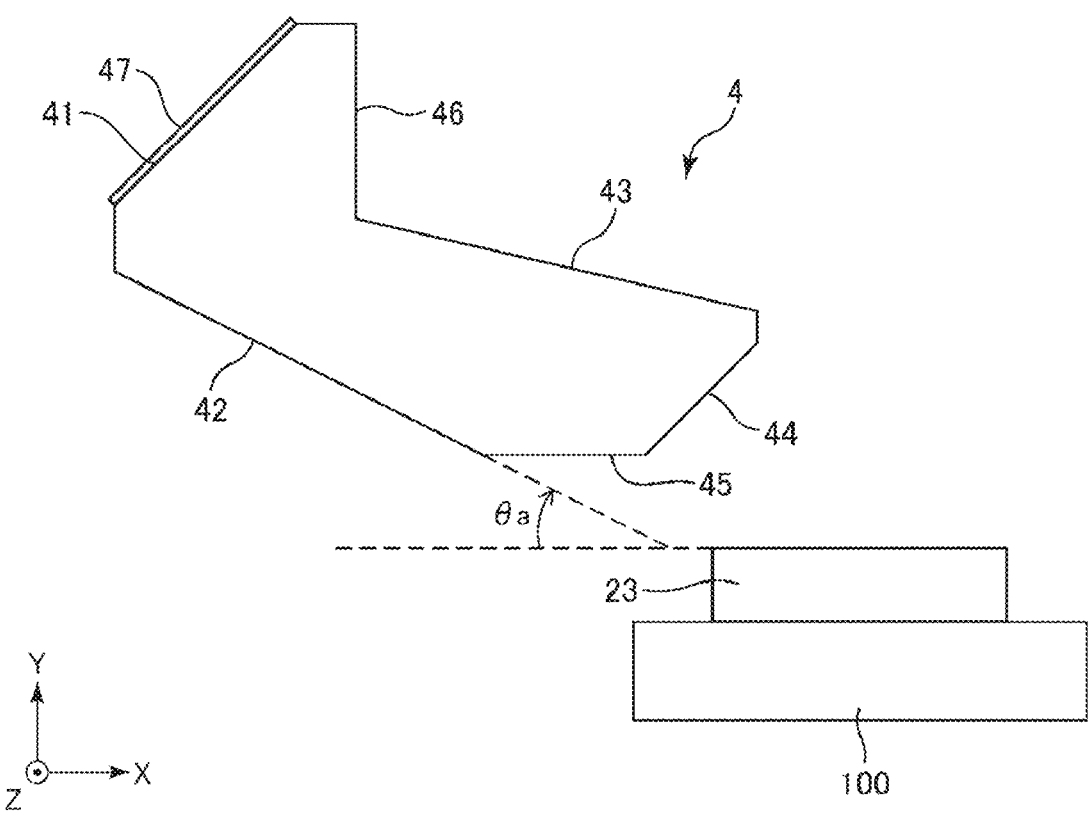
FIG. 5 is a side view of the prism of the biological fluid information acquisition apparatus shown in FIG. 1 as seen from the Z direction when an angle θa is 30°.
Figure 6:
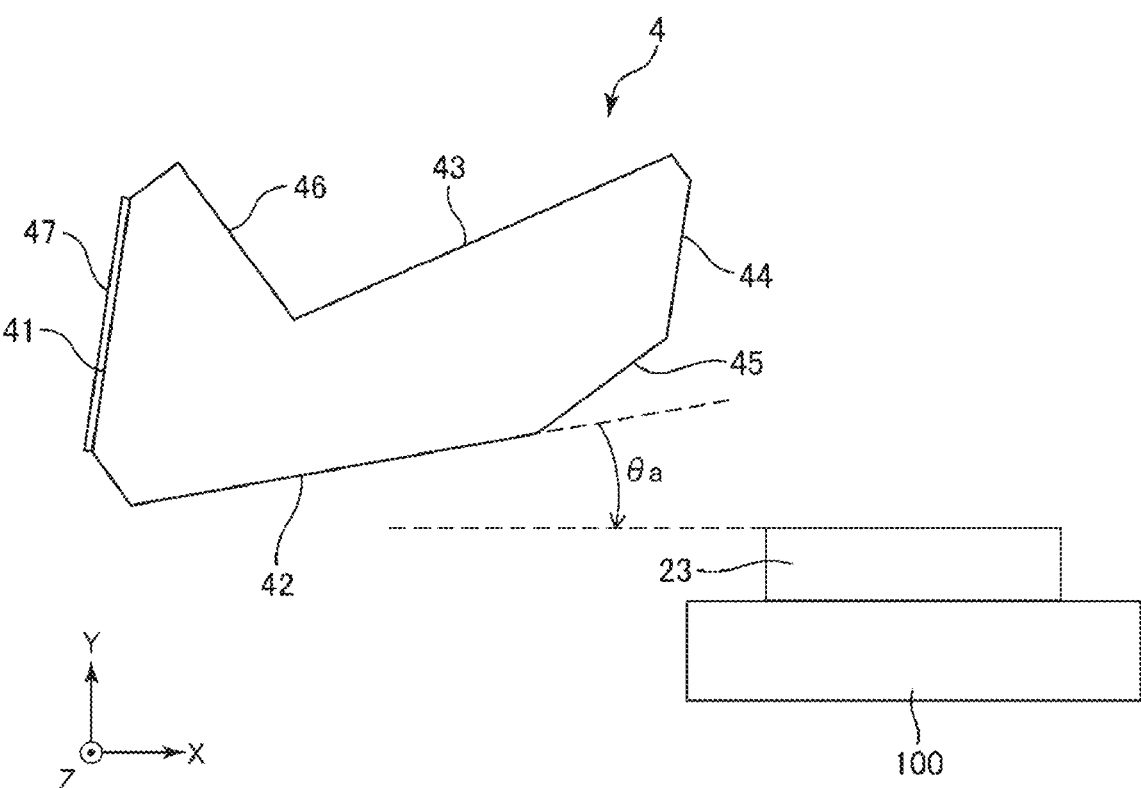
FIG. 6 is a side view of the prism of the biological fluid information acquisition apparatus shown in FIG. 1 as seen from the Z direction when the angle θa is −10°.
Figure 7:
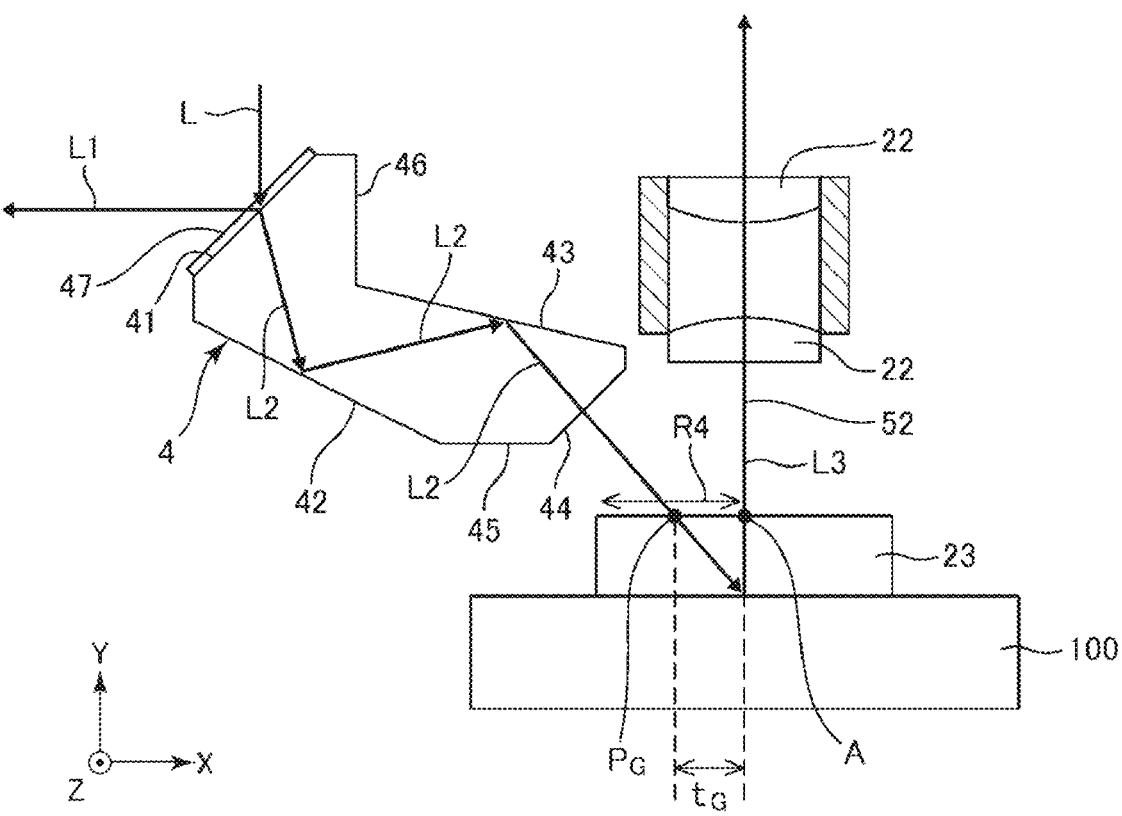
FIG. 7 is a side view of the prism of the biological fluid information acquisition apparatus shown in FIG. 1 as seen from the Z direction.
Figure 8:
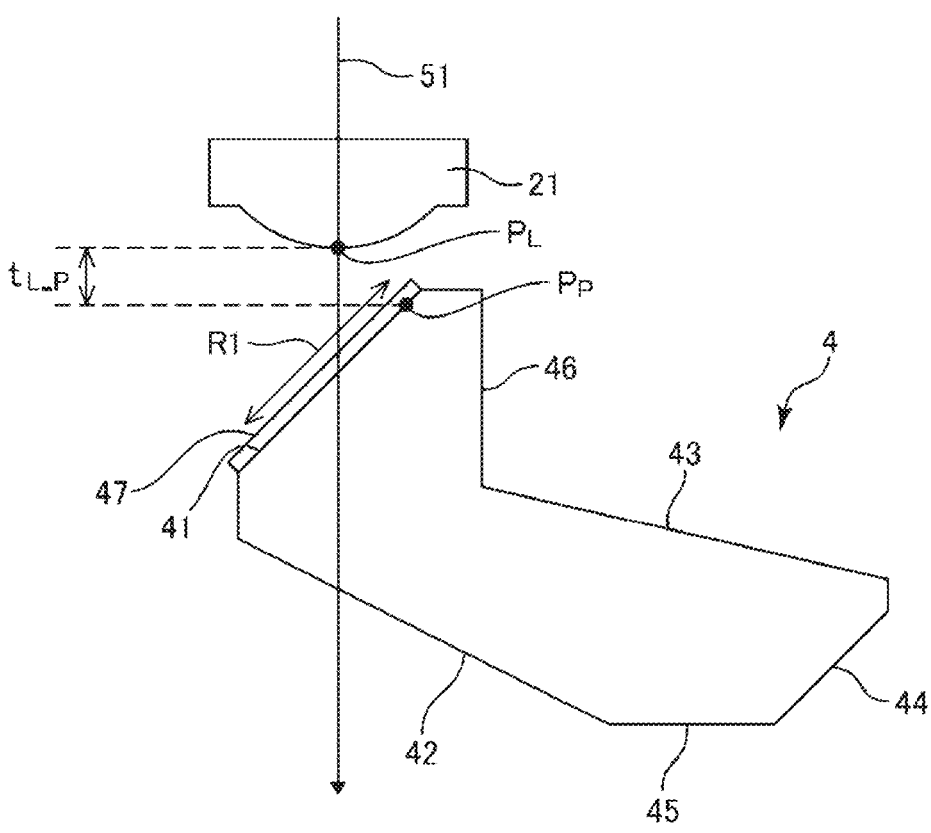
FIG. 8 is a side view of the prism of the biological fluid information acquisition apparatus shown in FIG. 1 as seen from the Z direction.
Figure 8:
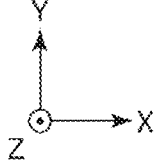

FIG. 1 shows a main part of a biological fluid information acquisition apparatus of the present disclosure in an embodiment. FIG. 2 is a block diagram of the biological fluid information acquisition apparatus shown in FIG. 1. FIG. 3 is a side view of a prism of the biological fluid information acquisition apparatus shown in FIG. 1 as seen from a Z direction. FIG. 4 is a side view of the prism of the biological fluid information acquisition apparatus shown in FIG. 1 as seen from the Z direction. FIG. 5 is a side view of the prism of the biological fluid information acquisition apparatus shown in FIG. 1 as seen from the Z direction when an angle θa is 30°. FIG. 6 is a side view of the prism of the biological fluid information acquisition apparatus shown in FIG. 1 as seen from the Z direction when the angle θa is −10°. FIG. 7 is a side view of the prism of the biological fluid information acquisition apparatus shown in FIG. 1 as seen from the Z direction. FIG. 8 is a side view of the prism of the biological fluid information acquisition apparatus shown in FIG. 1 as seen from the Z direction.

In the specification, for convenience of explanation, an upside in FIG. 1 is referred to as "upper" or "upward" and a downside is referred to as "lower" or "downward".

As shown in FIG. 1, as three axes orthogonal to one another, an X-axis, a Y-axis, and a Z-axis are shown. The pointer side of an arrow indicating each axis is "+: positive", and the tail side is "−: negative". Further, a direction parallel to the X-axis is also referred to as "X direction: X-axis direction", a direction parallel to the Y-axis is also referred to as "Y direction: Y-axis direction", and a direction parallel to the Z-axis is also referred to as "Z direction: Z-axis direction".

A width direction of a biological fluid information acquisition apparatus 1 is the X direction, a thickness direction of the biological fluid information acquisition apparatus 1 is the Y direction, and a length direction of the biological fluid information acquisition apparatus 1 is the Z direction.

In the individual drawings, as a laser beam L, a first luminous flux L1, a second luminous flux L2, and a scattered light L3, center lines of luminous fluxes, that is, rays of light are shown.

In FIG. 1, a housing 31 of the biological fluid information acquisition apparatus 1 is not entirely, but partially shown. In FIG. 2, only part of lines of each signal and each control is shown.

The biological fluid information acquisition apparatus 1 shown in FIG. 1 is an apparatus that acquires biological fluid information of a subject as a living body 100.

The biological fluid information is information on the fluid of the living body 100 including, for example, a blood flow volume, a blood volume, a blood flow velocity, a pulse rate, blood pressure, a pulse wave velocity, an arteriosclerosis level, and volume pulse wave in the living body 100.

The form of the biological fluid information acquisition apparatus 1 is not particularly limited, but includes various forms such as a form worn on a subject for use and a stationary form. In the embodiment, a case of application to a form worn on a subject for use is described.

As shown in FIGS. 1 and 2, the biological fluid information acquisition apparatus 1 includes a housing 31 that houses and supports the individual parts forming the biological fluid information acquisition apparatus 1. The housing 31 has a box shape and the outer shape thereof is a rectangular parallelepiped shape. Note that the shape of the housing 31 is not limited to that.

Further, the biological fluid information acquisition apparatus 1 includes a circuit board 2 having various electronic components, circuits, and the like. The circuit board 2 is disposed, that is, housed in the housing 31.

Furthermore, the biological fluid information acquisition apparatus 1 includes a light source 3 that emits a laser beam L, a first light receiving element 5, a second light receiving element 6, a differential circuit 7, a signal processing unit 8 that generates biological fluid information, a control unit 9 that controls driving of the biological fluid information acquisition apparatus 1, a storage unit 11 that stores various types of information, various programs, and the like, a display unit 12 that displays various types of information, and an operation unit 13 as an input unit for various kinds of instructions and various kinds of input. The light source 3, the first light receiving element 5, the second light receiving element 6, the differential circuit 7, the signal processing unit 8, the control unit 9, the storage unit 11, the display unit 12, and the operation unit 13 are each electrically coupled to the circuit board 2, and predetermined members thereof are disposed on the circuit board 2.

The biological fluid information acquisition apparatus 1 includes a prism 4, a collimating lens 21, a condensing lens 22, a cover glass 23 as a cover plate, and a light reflection member 24. The prism 4, the collimating lens 21, the condensing lens 22, and the light reflection member 24 are disposed, that is, housed in the housing 31. The cover glass 23 is disposed in a lower portion of the housing 31, that is, at an end of the housing 31 at the − side in the Y direction, supported by the housing 31, and exposed to the outside.

The circuit board 2 is disposed in an upper portion of the housing 31, that is, at an end of the housing 31 at the + side in the Y direction, and the light source 3, the first light receiving element 5, and the second light receiving element 6 are disposed in the upper portion of the housing 31. In this case, the first light receiving element 5 is disposed at the left side of the light source 3 in FIG. 1, that is, at the − side in the X direction, and the second light receiving element 6 is disposed at the right side of the light source 3 in FIG. 1, that is, at the + side in the X direction.

The prism 4 is disposed in the optical path between the light source 3 and the cover glass 23. The prism 4 has a function of branching the laser beam L emitted from the light source 3 into the first luminous flux L1 and the second luminous flux L2. The prism 4 and configurations relating to the prism 4 will be described later in detail.

The cover glass 23 is disposed at the − side in the Y direction of the second light receiving element 6, in the lower portion of the housing 31, that is, the end of the housing 31 at the − side in the Y direction. The cover glass 23 is a part that comes into contact with the living body 100 when the biological fluid information acquisition apparatus 1 is worn on the living body 100, and has a function of protecting the inside of the biological fluid information acquisition apparatus 1. The cover plate is not limited to the cover glass 23, and the constituent material thereof is not limited to the glass material, but includes a resin material or the like. The cover glass 23 may be separated from the living body 100 when the biological fluid information acquisition apparatus 1 is worn on the living body 100.

The cover glass 23 has a plate shape and has light transmissivity. The second luminous flux L2 emitted from a fourth boundary face 44 of the prism 4 is transmitted through the cover glass 23, and the scattered light L3 obtained from the living body 100 is transmitted through the cover glass 23.

The collimating lens 21 is disposed in the optical path between the light source 3 and a first boundary face 41 of the prism 4.

The condensing lens 22 is disposed in the optical path between the second light receiving element 6 and the cover glass 23.

The light reflection member 24 is disposed in the optical path between the first light receiving element 5 and the first boundary face 41 of the prism 4. The light reflection member 24 has a function of reflecting the first luminous flux L1 reflected by the first boundary face 41 toward the first light receiving element 5. Examples of the light reflection member 24 include a prism and a reflection plate.

The light source 3 has a function of emitting the laser beam L. The light source 3 is not particularly limited, and the examples thereof include a semiconductor laser.

The first light receiving element 5 has a function of receiving the first luminous flux L1. The first light receiving element 5 is not particularly limited, and the examples thereof include a photodiode and a phototransistor.

The second light receiving element 6 has a function of receiving the scattered light L3 obtained from the living body 100 when the second luminous flux L2 enters a site to be examined of the living body 100. The second light receiving element 6 is not particularly limited, and the examples thereof include a photodiode and a phototransistor.

The differential circuit 7 has a function of generating a light detection signal based on the output of the first light receiving element 5 and the second light receiving element 6. That is, the differential circuit 7 converts detection currents output from the first light receiving element 5 and the second light receiving element 6 into voltage signals, generates a signal corresponding to the difference between the voltage signals, and outputs the signal as a light detection signal.

The signal processing unit 8 includes, for example, an arithmetic circuit such as a CPU (central processing unit) and can be implemented as one or more processors, and reads and executes various programs and the like stored in the storage unit 11. The signal processing unit 8 generates biological fluid information by processing the light detection signal. A known method can be applied to the method of obtaining the biological fluid information based on the light detection signal, and the description thereof will be omitted.

The control unit 9 includes, for example, an arithmetic circuit such as a CPU (central processing unit) and can be implemented as one or more processors, and reads and executes various programs and the like stored in the storage unit 11. Thereby, control of the operation of the biological fluid information acquisition apparatus 1, various calculations, various determinations, and the like are performed.

The processors implementing the control unit 9, the signal processing unit 8, and the like may be provided separately or may be entirely or partially shared.

The storage unit 11 stores various programs executable by the control unit 9. The storage unit 11 can store various types of data input from the outside. The storage unit 11 includes a volatile memory such as a RAM (random access memory) and a nonvolatile memory such as a ROM (read only memory). The storage unit 11 is not limited to an undetachable type, but may include a detachable external storage device.

The display unit 12 is an example of a notification unit for notification of information and, for example, has a function of displaying various kinds of information including the biological fluid information. The display unit 12 is not particularly limited, and the examples thereof include a liquid crystal display device and an organic EL display device.

The operation unit 13 is not particularly limited, and the examples thereof include an operation button, an operation switch, and an operation dial. For example, a subject can give various kinds of instructions and various kinds of input to the biological fluid information acquisition apparatus 1 by operating the operation unit 13.

Instead of the display unit 12 and the operation unit 13, a display input unit having both functions of the display unit 12 and the operation unit 13 may be used together with the display unit 12 and the operation unit 13. For example, as the display input device, a touch panel can be used.

Next, the prism 4 and the configurations relating to the prism 4 will be described.

The prism 4 has the function of branching the laser beam L emitted from the light source 3 into the first luminous flux L1 and the second luminous flux L2.

The prism 4 is formed using various resin materials, various glass materials, or the like. The prism 4 may be integrally formed or may be formed using a plurality of members.

The prism 4 has a plate-like shape or a columnar shape. In the embodiment, the prism 4 has a shape as shown in FIGS. 1 and 3 as seen from the Z direction, and two surfaces of the prism 4 in the Z direction are planar surfaces. The two surfaces of the prism 4 in the Z direction may have other shapes.

As below, the individual conditions including the shape, the attitude, the placement, and the like of the prism 4 as seen from the Z direction will be described.

As shown in FIGS. 1 and 3, as seen from the Z direction, the prism 4 has the first boundary face 41, a second boundary face 42, a third boundary face 43, the fourth boundary face 44, a fifth boundary face 45, and a sixth boundary face 46 as boundaries with air. The individual boundary faces 41 to 46 are portions of the surfaces of the prism 4. The individual boundary faces 41 to 46 are planar surfaces and have linear shapes as seen from the Z direction. In the specification, the first boundary face 41 may be simply referred to as "boundary face 41", the second boundary face 42 may be simply referred to as "boundary face 42", the third boundary face 43 may be simply referred to as "boundary face 43", the fourth boundary face 44 may be simply referred to as "boundary face 44", the fifth boundary face 45 may be simply referred to as "boundary face 45", and the sixth boundary face 46 may be simply referred to as "boundary face 46".

The boundary face 41 of the prism 4 is a portion that branches the laser beam L emitted from the light source 3 into the first luminous flux L1 and the second luminous flux L2. That is, in the boundary face 41, the laser beam L is branched into the first luminous flux L1 reflected by the boundary face 41 and the second luminous flux L2 transmitted through the boundary face 41.

A polarization separation layer 47 is disposed on the boundary face 41. Accordingly, the first luminous flux L1 as the reflected light is S-polarized light, and the second luminous flux L2 as the transmitted light is P-polarized light. The polarization separation layer 47 may be omitted.

The boundary face 42 is a portion that totally reflects the second luminous flux L2 transmitted through the boundary face 41. The boundary face 43 is a portion that totally reflects the second luminous flux L2 reflected by the boundary face 42. The boundary face 44 is a portion from which the second luminous flux L2 reflected by the boundary face 43 is emitted. The boundary face 45 and the boundary face 46 are not used. In the drawings, as the laser beam L, the first luminous flux L1, and the second luminous flux L2, the center lines of the luminous fluxes, that is, rays of light are shown.

The individual boundary faces 41 to 46 are arranged clockwise from the boundary face 41 in the order of the boundary face 41, the boundary face 46, the boundary face 43, the boundary face 44, the boundary face 45, and the boundary face 42.

The boundary face 41 and the boundary face 44 are disposed to face each other. In the embodiment, the boundary face 41 and the boundary face 44 are parallel, however, may be non-parallel.

The boundary face 42 and the boundary face 43 are disposed to face each other. In the embodiment, the boundary face 42 and the boundary face 43 are non-parallel, however, may be parallel.

The boundary face 45 is disposed between the boundary face 42 and the boundary face 44. One end of the boundary face 45 is coupled to an end of the boundary face 42, and the other end of the boundary face 45 is coupled to an end of the boundary face 44. The part of the boundary face 45 of the prism 4 is not used. Since the boundary face 45 is provided and the shape of the prism 4 is formed as if a part of the prism 4 was cut out, the length of the prism 4 in the Y direction is shorter than that without the boundary face 45. Thereby, the thickness of the biological fluid information acquisition apparatus 1 can be made smaller and the size and the thickness of the biological fluid information acquisition apparatus 1 can be reduced.

The boundary face 46 is disposed between the boundary face 41 and the boundary face 43. One end of the boundary face 46 is coupled to an end of the boundary face 43. An angle θ formed between the boundary face 43 and the boundary face 46 at the prism 4 side is larger than 180°. Accordingly, the prism 4 is formed with a cutout portion as if cut out by the boundary face 43 and the boundary face 46, and thereby, the optical path in the prism 4 can be shortened. As a result, the thickness of the biological fluid information acquisition apparatus 1 can be made smaller, the width thereof can be smaller, and the size of the biological fluid information acquisition apparatus 1 can be reduced.

A width direction of the biological fluid information acquisition apparatus 1, that is, a width direction of the housing 31 is the X direction, and a thickness direction of the biological fluid information acquisition apparatus 1, that is, a thickness direction of the housing 31 orthogonal to the X direction is the Y direction. An interval between the boundary face 42 and the boundary face 43 in the Y direction is $t_{2\_3}$ as shown in the drawing, and an interval between the boundary face 41 and the boundary face 44 in the X direction is $t_{1\_4}$ as shown in the drawing. $t_{2\_3}$ is the distance between the boundary face 42 and the boundary face 43, and $t_{1\_4}$ is the distance between the boundary face 41 and the boundary face 44. According to the definitions, the interval between the boundary face 42 and the boundary face 43 in the Y direction, that is, the distance $t_{2\_3}$ is shorter than the interval between the boundary face 41 and the boundary face 44 in the X direction, that is, the distance $t_{1\_4}$. As a result, the length of the prism 4 in the Y direction can be shortened, and accordingly, the size of the biological fluid information acquisition apparatus 1 can be reduced, and in particular, the thickness thereof can be reduced. Thereby, the burden on the subject can be reduced.

According to the prism 4, the second luminous flux L2 reflected by the boundary face 43 can be prevented from being reflected by the boundary face 44 and returning within the prism 4 to the boundary face 41 side, and thereby, the biological fluid information can be accurately acquired.

As below, regarding the individual conditions of the prism 4, preferable conditions will be described, however, the conditions are not limited thereto.

When a beam diameter of the laser beam L emitted from the light source 3 is $D_0$, a beam diameter of the laser beam L in the boundary face 41 is $D_1$, a beam diameter of the second luminous flux L2 in the boundary face 42 is $D_2$, a beam diameter of the second luminous flux L2 in the boundary face 43 is $D_3$, an incidence angle of the laser beam L in the boundary face 41 is $\theta_1$, an incidence angle of the second luminous flux L2 in the boundary face 42 is $\theta_2$, and the distance between the boundary face 41 and the boundary face 44 is $t_{1\_4}$, the distance $t_{1\_4}$ satisfies the following expression (1).

$$\frac{2.2 \times D_0}{\sin(90° - \theta_1)} \frac{(D_2 + D_3)}{D_2 \cdot \tan(90° - \theta_2)} > t_{1\_4} > \frac{D_2}{2} + D_3 \qquad (1)$$

8

Accordingly, the second luminous flux L2 reflected by the boundary face 43 can be prevented from being reflected by the boundary face 44 and returning within the prism 4 to the boundary face 41 side, and thereby, the biological fluid information can be accurately acquired.

The beam diameter Do is the beam diameter after the collimating lens 21.

When the distance between the boundary face 42 and the boundary face 43 is $t_{2\_3}$, the distance $t_{2\_3}$ satisfies the following expression (2).

$$\frac{2.2 \times D_0}{\sin(90° - \theta_1)} > t_{2\_3} > \frac{D_2}{2}\tan(90° - \theta_2) \qquad (2)$$

As a result, the length of the prism 4 in the Y direction can be shortened, and accordingly, the size of the biological fluid information acquisition apparatus 1 can be reduced, and in particular, the thickness thereof can be reduced.

The beam diameter $D_1$ of the laser beam L in the boundary face 41 is expressed by the following expression (5).

$$D_1 = D_0/\sin(90 - \theta_1) \qquad (5)$$

When a refractive index of the prism 4 is $n_t$, a refractive index of air is $n_i$, and an incidence angle of the second luminous flux L2 in the boundary face 43 is $\theta_3$, a relationship $\theta_2 \leq \theta_3$ is satisfied. Thereby, the length of the prism 4 in the Y direction can be shortened.

The incidence angle $\theta_2$ satisfies the following expression (3).

$$\mathrm{atan}\left(\frac{D_2}{2 \cdot \dfrac{2.2 \times D_0}{\sin(90° - \theta_1)}}\right) > \theta_2 > \mathrm{asin}\left(\frac{n_i}{n_t}\right) \qquad (3)$$

The incidence angle $\theta_3$ satisfies the following expression (4).

$$\mathrm{atan}\left(\frac{D_2}{2 \cdot \dfrac{2.2 \times D_0}{\sin(90° - \theta_1)}}\right) > \theta_3 > \mathrm{asin}\left(\frac{n_i}{n_t}\right) \qquad (4)$$

Accordingly, an angle around 45° can be realized as the incidence angle of the second luminous flux L2 on the living body 100, the reflected light can be suppressed from being taken in by the cover glass 23, and thereby, the biological fluid information can be accurately acquired. In addition, the length of the prism 4 in the Y direction can be shortened, and accordingly, the size of the biological fluid information acquisition apparatus 1 can be reduced, and in particular, the thickness thereof can be reduced.

Here, when $\theta_2$ is equal to or less than the value of the right side in the expression (3), total reflection does not occur at the boundary face 42 depending on the other conditions.

When $\theta_2$ is equal to or greater than the value of the left side in the expression (3), the prism 4 becomes larger depending on the other conditions.

When $\theta_3$ is equal to or less than the value of the right side in the expression (4), total reflection does not occur at the boundary face 43 depending on the other conditions.

When $\theta_3$ is equal to or larger than the value of the left side in the expression (4), the prism 4 becomes larger depending on the other conditions.

Further, as shown in FIG. 4, a line segment Q connecting a center P1 of the second luminous flux L2 in the boundary face 42 and a center P2 of the second luminous flux L2 in the boundary face 43 as seen from the Z direction is assumed. In this case, the center P1 is the center of an incidence range R2 in the boundary face 42 of the second luminous flux L2, and the center P2 is the center of an incidence range R3 in the boundary face 43 of the second luminous flux L2.

A component QY of the line segment Q in the Y direction is shorter than a component QX of the line segment Q in the X direction. As a result, the length of the prism 4 in the Y direction can be shortened, and accordingly, the size of the biological fluid information acquisition apparatus 1 can be reduced, and in particular, the thickness thereof can be reduced.

The attitude of the prism 4 in the biological fluid information acquisition apparatus 1 is not particularly limited, but is appropriately set according to the conditions. In the embodiment, as shown in FIGS. 5 and 6, as seen from the Z direction, an angle θa of the second boundary face 42 with respect to the cover glass 23 is from −10° to 30°. Thereby, the thickness of the biological fluid information acquisition apparatus 1 can be reduced. The angle θa is a value with reference to the surface of the cover glass 23.

FIG. 5 shows a case where the angle θa is +30°, FIG. 6 shows a case where the angle θa is −10°, and the attitude of the prism 4 with respect to the cover glass 23 can be set within the above described range. Therefore, for example, the angle θa can be set to zero, that is, the attitude of the prism 4 can be set to an attitude such that the second boundary face 42 and the surface of the cover glass 23 are parallel to each other.

As shown in FIG. 7, the position of a center $P_G$ of the second luminous flux L2 entering the cover glass 23 in the incident surface of the cover glass 23 is located closer to the prism 4 than an optical axis 52 of the condensing lens 22. In other words, the center $P_G$ is the center of an incidence range R4 in the cover glass 23 of the second luminous flux L2. Accordingly, the use efficiency of the scattered light L3 obtained from the site to be examined of the living body 100 can be increased.

Further, a distance to between the center PG and a position A in the incident surface of the cover glass 23 of the optical axis 52 is more than 0 and equal to or less than 2 mm. Accordingly, the use efficiency of the scattered light L3 obtained from the site to be examined of the living body 100 can be increased. The distance to is more preferably from 0.25 mm to 2 mm. Accordingly, the use efficiency of the scattered light L3 obtained from the site to be examined of the living body 100 can be further increased.

As shown in FIG. 8, as seen from the Z direction, a point located closest to the collimating lens 21 in an incidence range R1 in the boundary face 41 of the laser beam L emitted from the light source 3 is $P_P$. A vertex of the collimating lens 21 on a side of the boundary face 41 is $P_L$.

A distance $t_{L\_P}$ between the point $P_P$ and the vertex $P_L$ in a direction of an optical axis 51 of the collimating lens 21 is more than 0.

Thereby, an interference of the first luminous flux L1 reflected by the boundary face 41 with the collimating lens 21 can be prevented.

Next, a procedure for acquiring biological fluid information by the biological fluid information acquisition apparatus 1 and an operation of the biological fluid information acquisition apparatus 1 will be described with reference to FIGS. 1 and 2.

First, the subject wears the biological fluid information acquisition apparatus 1 on the living body 100 so that the cover glass 23 of the biological fluid information acquisition apparatus 1 is placed at the site to be examined of the living body 100.

When the laser beam L is emitted from the light source 3, the laser beam L is parallelized by the collimating lens 21, enters the boundary face 41 of the prism 4, and is branched into the first luminous flux L1 and the second luminous flux L2 in the boundary face 41. That is, the laser beam L is branched into the first luminous flux L1 reflected by the boundary face 41 and the second luminous flux L2 transmitted through the boundary face 41.

The first luminous flux L1 is reflected by the light reflection member 24, enters the first light receiving element 5, and is received by the first light receiving element 5. A detection current corresponding to the amount of received light is output from the first light receiving element 5 to the differential circuit 7.

The second luminous flux L2 is reflected by the boundary face 42, reflected by the boundary face 43, emitted from the boundary face 44, transmitted through the cover glass 23, and enters, that is, is applied to the site to be examined of the living body 100. Accordingly, the scattered light L3 is emitted from the site to be examined of the living body 100.

The scattered light L3 obtained from the site to be examined of the living body 100 is collected by the condensing lens 22, enters the second light receiving element 6, and is received by the second light receiving element 6. A detection current corresponding to the amount of received light is output from the second light receiving element 6 to the differential circuit 7.

The differential circuit 7 converts the detection currents output from the first light receiving element 5 and the second light receiving element 6 into voltage signals, generates a signal corresponding to the difference between the voltage signals, and outputs the signal as a light detection signal to the signal processing unit 8.

The signal processing unit 8 generates predetermined biological fluid information by processing the light detection signal. Examples of the biological fluid information include a blood flow volume, a blood volume, a blood flow velocity, a pulse rate, blood pressure, a pulse wave velocity, an arteriosclerosis level, and volume pulse wave.

The acquired biological fluid information is stored in the storage unit 11 and read as necessary.

Further, the acquired biological fluid information is displayed by the display unit 12. Thus, the subject can recognize the biological fluid information.

As described above, according to the biological fluid information acquisition apparatus 1, the length of the prism 4 in the Y direction can be shortened using the above described prism 4, and accordingly, the size of the biological fluid information acquisition apparatus 1 can be reduced, and in particular, the thickness thereof can be reduced. Thereby, the burden on the subject can be reduced.

In addition, the second luminous flux L2 reflected by the boundary face 43 of the prism 4 can be prevented from being reflected by the boundary face 44 and returning within the prism 4 to the boundary face 41 side, and thereby, the biological fluid information can be accurately acquired.

Other Configurations

The biological fluid information acquisition apparatus 1 may have the following configurations, and the configurations may be applied to the above described embodiment.

Configuration 1

Of the laser beam L emitted from the light source 3, a predetermined amount, for example, 3% of the laser beam L may be reflected by the first boundary face 41 of the prism 4 and entered into a reference light receiving element as a reference light. Accordingly, the S/N ratio of the light detection signal can be improved, and thus the biological fluid information can be acquired with higher accuracy.

When a plate-like optical branching element is used instead of the prism 4, it is necessary to consider not only the reflected light by the front surface of the optical branching element but also the reflected light by the back surface of the branching element and a light amount adjustment mechanism is required. However, in the embodiment, the prism 4 is used and the light amount adjustment mechanism is not required and the configuration can be simplified.

Configuration 2

The first boundary face 41 of the prism 4 may be provided with a light shielding portion having an opening that allows a part of the laser beam L emitted from the light source 3 to pass therethrough and blocks the remaining part. The light shielding portion can be formed by, for example, pinhole processing or the like.

Configuration 3

At least a part of the differential circuit 7 may be configured with a circuit having a differential amplifier or the like, and a light detection signal may be generated by the circuit.

Configuration 4

At least a part of the differential circuit 7 may be configured with an arithmetic processing unit that performs arithmetic processing, and a light detection signal may be calculated by arithmetic processing such as subtraction using the arithmetic processing unit.

As described above, the biological fluid information acquisition apparatus 1 includes the light source 3 that emits the laser beam L, the prism 4 that branches the laser beam L emitted from the light source 3 into the first luminous flux L1 and the second luminous flux L2, the first light receiving element 5 that receives the first luminous flux L1, the second light receiving element 6 that receives the scattered light L3 obtained from the living body 100 when the second luminous flux L2 enters the site to be examined of the living body 100, the differential circuit 7 that generates the light detection signal based on the output of the first light receiving element 5 and the second light receiving element 6, and the signal processing unit 8 that generates the biological fluid information by processing the light detection signal.

The prism 4 has the plate-like shape or the columnar shape. The prism 4 has the first boundary face 41 that branches the laser beam L emitted from the light source 3 into the first luminous flux L1 and the second luminous flux L2, the second boundary face 42 that totally reflects the second luminous flux L2, the third boundary face 43 that totally reflects the second luminous flux L2 reflected by the second boundary face 42, and the fourth boundary face 44 that emits the second luminous flux L2 reflected by the third boundary face 43.

When the width direction of the biological fluid information acquisition apparatus 1 is the X direction, and the thickness direction of the biological fluid information acquisition apparatus 1 orthogonal to the X direction is the Y direction, the interval between the second boundary face 42 and the third boundary face 43 in the Y direction is shorter than the interval between the first boundary face 41 and the fourth boundary face 44 in the X direction.

According to the biological fluid information acquisition apparatus 1, the length of the prism 4 in the Y direction can be shortened, and accordingly, the size of the biological fluid information acquisition apparatus 1 can be reduced, and in particular, the thickness thereof can be reduced. Thereby, the burden on the subject can be reduced.

In addition, the second luminous flux L2 reflected by the third boundary face 43 can be prevented from being reflected by the fourth boundary face 44 and returning within the prism 4 to the first boundary face 41 side, and thereby, the biological fluid information can be accurately acquired.

In the biological fluid information acquisition apparatus 1, when the beam diameter of the laser beam L emitted from the light source 3 is Do, the beam diameter of the second luminous flux L2 in the second boundary face 42 is $D_2$, the beam diameter of the second luminous flux L2 in the third boundary face 43 is $D_3$, the incidence angle of the laser beam L in the first boundary face 41 is $\theta_1$, the incidence angle of the second luminous flux L2 in the second boundary face 42 is $\theta_2$, and the distance between the first boundary face 41 and the fourth boundary face 44 is $t_{1\_4}$, the distance $t_{1\_4}$ satisfies the following expression (1).

$$\frac{2.2 \times D_0}{\sin(90° - \theta_1)} \frac{(D_2 + D_3)}{D_2 \cdot \tan(90° - \theta_2)} > t_{1\_4} > \frac{D_2}{2} + D_3 \qquad (1)$$

Accordingly, the second luminous flux L2 reflected by the third boundary face 43 can be prevented from being reflected by the fourth boundary face 44 and returning within the prism 4 to the first boundary face 41 side, and thereby, the biological fluid information can be accurately acquired.

In the biological fluid information acquisition apparatus 1, when the beam diameter of the laser beam L emitted from the light source 3 is $D_0$, the beam diameter of the second luminous flux L2 in the second boundary face 42 is $D_2$, the incidence angle of the laser beam L in the first boundary face 41 is $\theta_1$, the incidence angle of the second luminous flux L2 in the second boundary face 42 is $\theta_2$, and the distance between the second boundary face 42 and the third boundary face 43 is $t_{2\_3}$, the distance $t_{2\_3}$ satisfies the following expression (2).

$$\frac{2.2 \times D_0}{\sin(90° - \theta_1)} > t_{2\_3} > \frac{D_2}{2} \tan(90° - \theta_2) \qquad (2)$$

As a result, the length of the prism 4 in the Y direction can be shortened, and accordingly, the size of the biological fluid information acquisition apparatus 1 can be reduced, and in particular, the thickness thereof can be reduced.

In the biological fluid information acquisition apparatus 1, when the direction orthogonal to the X direction and the Y direction is the Z direction, the component QY in the Y direction of the line segment Q connecting the center P1 of the second luminous flux L2 in the second boundary face 42 and the center P2 of the second luminous flux L2 in the third boundary face 43 is shorter than the component QX in the X direction of the line segment Q as seen from the Z direction.

As a result, the length of the prism 4 in the Y direction can be shortened, and accordingly, the size of the biological fluid information acquisition apparatus 1 can be reduced, and in particular, the thickness thereof can be reduced.

Further, the biological fluid information acquisition apparatus 1 includes the housing 31 that houses the prism 4, and the cover glass 23 as the cover plate that is disposed in the housing 31 and through which the second luminous flux L2 emitted from the fourth boundary face 44 is transmitted. The angle θa of the second boundary face 42 with respect to the cover glass 23 is from −10° to 30°. Thereby, the thickness of the biological fluid information acquisition apparatus 1 can be reduced.

In the biological fluid information acquisition apparatus 1, when the refractive index of the prism 4 is $n_t$, the refractive index of air is $n_i$, the beam diameter of the laser beam L emitted from the light source 3 is $D_0$, the beam diameter of the second luminous flux L2 in the second boundary face 42 is $D_2$, the incidence angle of the laser beam L in the first boundary face 41 is $\theta_1$, the incidence angle of the second luminous flux L2 in the second boundary face 42 is $\theta_2$, and the incidence angle of the second luminous flux L2 in the third boundary face 43 is $\theta_3$, the incidence angle $\theta_2$ satisfies s the following expression (3), the incidence angle $\theta_3$ satisfies the following expression (4), and $\theta_2 \leq \theta_3$.

$$\mathrm{atan}\left(\frac{D_2}{2 \cdot \frac{2.2 \times D_0}{\sin(90° - \theta_1)}}\right) > \theta_2 > \mathrm{asin}\left(\frac{n_i}{n_t}\right) \quad (3)$$

$$\mathrm{atan}\left(\frac{D_2}{2 \cdot \frac{2.2 \times D_0}{\sin(90° - \theta_1)}}\right) > \theta_3 > \mathrm{asin}\left(\frac{n_i}{n_t}\right) \quad (4)$$

Accordingly, an angle around 45° can be realized as the incidence angle of the second luminous flux L2 on the living body 100, the reflected light can be suppressed from being taken in by the cover glass 23, and thereby, the biological fluid information can be accurately acquired. In addition, the length of the prism 4 in the Y direction can be shortened, and accordingly, the size of the biological fluid information acquisition apparatus 1 can be reduced, and in particular, the thickness thereof can be reduced.

The biological fluid information acquisition apparatus 1 includes the housing 31 that houses the prism 4, the condensing lens 22 that is disposed in the housing 31 and collects the scattered light L3 in the second light receiving element 6, and the cover glass 23 as the cover plate that is disposed in the housing 31 and through which the second luminous flux L2 emitted from the fourth boundary face 44 is transmitted. When the direction orthogonal to the X direction and the Y direction is the Z direction, as seen from the Z direction, the position of the center PG in the cover glass 23 of the second luminous flux L2 entering the cover glass 23 is located closer to the prism 4 than the optical axis 52 of the condensing lens 22, and the distance to between the center PG and the position A of the optical axis 52 in the cover glass 23 is more than 0 and equal to or less than 2 mm.

Accordingly, the use efficiency of the scattered light L3 obtained from the site to be examined of the living body 100 can be increased.

The biological fluid information acquisition apparatus 1 includes the collimating lens 21 that is disposed between the light source 3 and the first boundary face 41 and through which the laser beam L emitted from the light source 3 is transmitted. Further, when the direction orthogonal to the X direction and the Y direction is the Z direction, in the incidence range R1 in the first boundary face 41 of the laser beam L emitted from the light source 3, the distance $t_{L\_P}$ in the optical axis 51 direction of the collimating lens 21 between the point $P_P$ located closest to the collimating lens 21 and the vertex $P_L$ of the collimating lens 21 at the first boundary face 41 side is more than 0 as seen from the Z direction.

Thereby, an interference of the first luminous flux L1 reflected by the first boundary face 41 with the collimating lens 21 can be prevented.

In the biological fluid information acquisition apparatus 1, when the direction orthogonal to the X direction and the Y direction is the Z direction, the prism 4 has the fifth boundary face 45 between the second boundary face 42 and the fourth boundary face 44 as seen from the Z direction.

Since the boundary face 45 is provided and the shape of the prism 4 is formed as if a part of the prism 4 was cut out, the length of the prism 4 in the Y direction is shorter than that without the boundary face 45. Thereby, the thickness of the biological fluid information acquisition apparatus 1 can be made smaller and the size and the thickness of the biological fluid information acquisition apparatus 1 can be reduced.

As above, the biological fluid information acquisition apparatus of the present disclosure is described based on the illustrated embodiments, however, the present disclosure is not limited thereto. The configurations of the respective portions can be replaced by any configurations having the same functions. Further, any other configuration may be added.

What is claimed is:

1. A biological fluid information acquisition apparatus comprising:
   a light source emitting a laser beam;
   a prism branching the laser beam emitted from the light source into a first luminous flux and a second luminous flux;
   a first light receiving element receiving the first luminous flux;
   a second light receiving element receiving a scattered light obtained from a living body when the second luminous flux enters a site to be examined of the living body;
   a differential circuit generating a light detection signal based on output of the first light receiving element and the second light receiving element; and
   a signal processing unit generating biological fluid information by processing the light detection signal, wherein
   the prism has a plate-like shape or a columnar shape,
   the prism has a first boundary face that branches the laser beam emitted from the light source into the first luminous flux and the second luminous flux, a second boundary face that totally reflects the second luminous flux, a third boundary face that totally reflects the second luminous flux reflected by the second boundary face, and a fourth boundary face emitting the second luminous flux reflected by the third boundary face, and
   when a width direction of the biological fluid information acquisition apparatus is an X direction and a thickness direction of the biological fluid information acquisition apparatus orthogonal to the X direction is a Y direction, an interval between the second boundary face and the third boundary face in the Y direction is shorter than an interval between the first boundary face and the fourth boundary face in the X direction.

2. The biological fluid information acquisition apparatus according to claim 1, wherein
   when a beam diameter of the laser beam emitted from the light source is $D_0$, a beam diameter of the second luminous flux in the second boundary face is $D_2$, a beam diameter of the second luminous flux in the third boundary face is $D_3$, an incidence angle of the laser beam in the first boundary face is $\theta_1$, an incidence angle of the second luminous flux in the second boundary face is $\theta_2$, and a distance between the first boundary face and the fourth boundary face is $t_{1\_4}$, the distance $t_{1\_4}$ satisfies a following expression (1).

$$\frac{2.2 \times D_0}{\sin(90° - \theta_1)} \frac{(D_2 + D_3)}{D_2 \cdot \tan(90° - \theta_2)} > t_{1\_4} > \frac{D_2}{2} + D_3 \qquad (1)$$

3. The biological fluid information acquisition apparatus according to claim 1, wherein
  when a beam diameter of the laser beam emitted from the light source is $D_0$, a beam diameter of the second luminous flux in the second boundary face is $D_2$, an incidence angle of the laser beam in the first boundary face is $\theta_1$, an incidence angle of the second luminous flux in the second boundary face is $\theta_2$, and a distance between the second boundary face and the third boundary face is $t_{2\_3}$, the distance $t_{2\_3}$ satisfies a following expression (2).

$$\frac{2.2 \times D_0}{\sin(90° - \theta_1)} > t_{2\_3} > \frac{D_2}{2}\tan(90° - \theta_2) \qquad (2)$$

4. The biological fluid information acquisition apparatus according to claim 1, wherein
  when a direction orthogonal to the X direction and the Y direction is a Z direction, a component in the Y direction of a line segment connecting a center of the second luminous flux in the second boundary face and a center of the second luminous flux in the third boundary face is shorter than a component in the X direction of the line segment as seen from the Z direction.

5. The biological fluid information acquisition apparatus according to claim 1, further comprising:
  a housing housing the prism; and
  a cover plate disposed in the housing, through which the second luminous flux emitted from the fourth boundary face is transmitted, wherein
  an angle of the second boundary face with respect to the cover plate is from −10° to 30°.

6. The biological fluid information acquisition apparatus according to claim 1, wherein
  when a refractive index of the prism is $n_t$, a refractive index of air is $n_i$, a beam diameter of the laser beam emitted from the light source is $D_0$, a beam diameter of the second luminous flux in the second boundary face is $D_2$, an incidence angle of the laser beam in the first boundary face is $\theta_1$, an incidence angle of the second luminous flux in the second boundary face is $\theta_2$, and an incidence angle of the second luminous flux in the third boundary face is $\theta_3$, the incidence angle $\theta_2$ satisfies a following expression (3), the incidence angle $\theta_3$ satisfies a following expression (4), and $\theta_2 \leq \theta_3$.

$$\operatorname{atan}\left(\frac{D_2}{2 \cdot \dfrac{2.2 \times D_0}{\sin(90° - \theta_1)}}\right) > \theta_2 > \operatorname{asin}\left(\frac{n_i}{n_t}\right) \qquad (3)$$

$$\operatorname{atan}\left(\frac{D_2}{2 \cdot \dfrac{2.2 \times D_0}{\sin(90° - \theta_1)}}\right) > \theta_3 > \operatorname{asin}\left(\frac{n_i}{n_t}\right) \qquad (4)$$

7. The biological fluid information acquisition apparatus according to claim 1, further comprising:
  a housing housing the prism;
  a condensing lens disposed in the housing and collecting the scattered light in the second light receiving element; and
  a cover plate disposed in the housing, through which the second luminous flux emitted from the fourth boundary face is transmitted, wherein
  when a direction orthogonal to the X direction and the Y direction is a Z direction, as seen from the Z direction, a position in the cover plate of a center of the second luminous flux entering the cover plate is located closer to the prism than an optical axis of the condensing lens, and
  a distance between the center and a position of the optical axis in the cover plate is more than 0 and equal to or less than 2 mm.

8. The biological fluid information acquisition apparatus according to claim 1, further comprising a collimating lens disposed between the light source and the first boundary face, through which the laser beam emitted from the light source is transmitted, wherein
  when a direction orthogonal to the X direction and the Y direction is a Z direction, in an incidence range in the first boundary face of the laser beam emitted from the light source, a distance in a direction of an optical axis of the collimating lens between a point located closest to the collimating lens and a vertex of the collimating lens on a side of the first boundary face is more than 0 as seen from the Z direction.

9. The biological fluid information acquisition apparatus according to claim 1, wherein
  when a direction orthogonal to the X direction and the Y direction is a Z direction, the prism has a fifth boundary face between the second boundary face and the fourth boundary face as seen from the Z direction.

* * * * *